(12) United States Patent
Yamawaki et al.

(10) Patent No.: US 9,029,588 B2
(45) Date of Patent: May 12, 2015

(54) METHOD FOR MANUFACTURING REFINED CHLOROGENIC ACIDS COMPOSITION

(75) Inventors: Kenji Yamawaki, Narita (JP); Yukiteru Sugiyama, Narita (JP); Hitoshi Sato, Narita (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 14/128,325

(22) PCT Filed: Jun. 21, 2012

(86) PCT No.: PCT/JP2012/065875
§ 371 (c)(1),
(2), (4) Date: Dec. 20, 2013

(87) PCT Pub. No.: WO2012/176845
PCT Pub. Date: Dec. 27, 2012

(65) Prior Publication Data
US 2014/0135391 A1    May 15, 2014

(30) Foreign Application Priority Data
Jun. 21, 2011 (JP) ................................ 2011-136928

(51) Int. Cl.
| | | |
|---|---|---|
| *A61K 31/216* | (2006.01) | |
| *A23F 5/22* | (2006.01) | |
| *B01J 39/04* | (2006.01) | |
| *B01J 41/04* | (2006.01) | |
| *B01J 47/02* | (2006.01) | |
| *B01J 20/20* | (2006.01) | |
| *A61K 36/74* | (2006.01) | |
| *C02F 1/76* | (2006.01) | |
| *A23L 1/30* | (2006.01) | |
| *C07C 67/56* | (2006.01) | |
| *C02F 1/42* | (2006.01) | |

(52) U.S. Cl.
CPC ............... *A61K 31/216* (2013.01); *A23F 5/223* (2013.01); *C07C 2101/14* (2013.01); *B01J 39/043* (2013.01); *B01J 39/046* (2013.01); *B01J 41/043* (2013.01); *B01J 41/046* (2013.01); *B01J 47/026* (2013.01); *B01J 20/20* (2013.01); *C02F 1/42* (2013.01); *A61K 36/74* (2013.01); *C02F 1/76* (2013.01); *A23L 1/3002* (2013.01); *C07C 67/56* (2013.01)

(58) Field of Classification Search
None
See application file for complete search history.

(56) References Cited

U.S. PATENT DOCUMENTS

2009/0053381 A1 * 2/2009 Fukuda et al. ............... 426/595

FOREIGN PATENT DOCUMENTS

| CN | 101288485 A | 10/2008 |
|---|---|---|
| JP | 58-138347 | 8/1983 |
| JP | 4 36148 | 2/1992 |
| JP | 4 145048 | 5/1992 |
| JP | 4 145049 | 5/1992 |
| JP | 2004 194515 | 7/2004 |
| JP | 2005 245307 | 9/2005 |
| JP | 2005-263632 | 9/2005 |
| JP | 2006 174746 | 7/2006 |
| JP | 2008 94758 | 4/2008 |
| JP | 2008 266144 | 11/2008 |

OTHER PUBLICATIONS

International Preliminary Report on Patentability and Written Opinion issued Jan. 9, 2014 in PCT/JP2012/065875 (submitting English translation only).
Yichen Luo et al., "Screening of Conditions for Refining Chlorogenic Acid from Eucommia Folium Using Ion Exchange Resin", Science & Technology Information, No. 14, Dec. 31, 2010, pp. 252-253 (with English Translation).
International Search Report Issued Sep. 4, 2012 in PCT/JP12/065875 Filed Jun. 21, 2012.

* cited by examiner

*Primary Examiner* — Karl J Puttlitz
(74) *Attorney, Agent, or Firm* — Oblon, McClelland, Maier & Neustadt, L.L.P.

(57) ABSTRACT

Provided is a method for producing a chlorogenic acids composition having a reduced caffeine content and good taste and favor, capable of efficiently recovering high purity of chlorogenic acids from a chlorogenic acids-containing composition. The method for producing a purified chlorogenic acids composition comprises a step A of bringing a chlorogenic acids-containing composition into contact with a cation exchange resin; a step B of bringing the liquid obtained in the step A into contact with an anion exchange resin; and a step C of bringing an eluent into contact with the anion exchange resin after the step B.

13 Claims, No Drawings

METHOD FOR MANUFACTURING REFINED CHLOROGENIC ACIDS COMPOSITION

CROSS REFERENCE TO RELATED APPLICATION

This application is a 371 of PCT/JP2012/065875, filed on Jun. 21, 2012, and claims priority to Japanese Patent Application No. 2011-136928, filed on Jun. 21, 2011.

FIELD OF THE INVENTION

The present invention relates to a method for producing a purified chlorogenic acids composition.

BACKGROUND OF THE INVENTION

Chlorogenic acids, which have been reported to have excellent antihypertensive effect, are desired to be applied to a wide variety of uses including supplements and food and drink (Patent Document 1).

As a material containing a large amount of chlorogenic acids, green coffee beans are mentioned; however, green coffee beans contain caffeine, which causes harmful effects such as insomnia and hypersensitivity if excessively taken. Because of this, a method for selectively removing caffeine from a chlorogenic acids-containing composition which contains caffeine, has been investigated.

In a method for extracting chlorogenic acids from green coffee beans, it is known to remove caffeine by bringing an extract of green coffee beans with an aqueous solvent into contact with strongly acidic cation exchange resin (Patent Document 2).

Furthermore, as a method for obtaining a chlorogenic acids composition containing chlorogenic acids at high concentrations and a reduced amount of caffeine, a method of adsorbing and separating chlorogenic acids by bringing a coffee-bean extract into contact with a hydrophobic adsorbent such as a styrene-divinylbenzene-based synthetic adsorbent is known (Patent Documents 3, 4).

CITATION LIST

Patent Document

[Patent Document 1] JP-A-2004-194515
[Patent Document 2] JP-A-4-145048
[Patent Document 3] JP-A-2008-94758
[Patent Document 4] JP-A-4-145049

SUMMARY OF THE INVENTION

The present invention provides a method for producing a purified chlorogenic acids composition, comprising a step A of bringing a chlorogenic acids-containing composition into contact with a cation exchange resin; a step B of bringing the liquid obtained in the step A into contact with an anion exchange resin; and a step C of bringing an eluent into contact with the anion exchange resin after the step B.

Furthermore, the present invention provides a purified chlorogenic acids composition in which the ratio (mass ratio) of protein/chlorogenic acids is 0.1 or smaller, the ratio (mass ratio) of citric acid/chlorogenic acids is 0.05 or larger, and chlorogenic acids are contained in an amount of 60 mass % or larger in solids.

DETAILED DESCRIPTION OF THE INVENTION

The present inventors studied, with a view toward applying chlorogenic acids to a wide variety of uses, on a method for producing a purified chlorogenic acids composition. As a result, they found that if a strongly acidic cation exchange resin is used (Patent Document 2), a large amount of resin is required in order to increase the purity of chlorogenic acids and the removal rate of caffeine, and that if the use amount of cation exchange resin is reduced, the purity of the chlorogenic acids obtained and the removal rate of caffeine are low and taste and flavor of chlorogenic acids are unsatisfactory. In the method of Patent Document 3, the amount of caffeine is reduced; however, the yield of a chlorogenic acids composition is low. Thus, further improvement was required. They found that, in the method of Patent Document 4 in which chlorogenic acid and caffeine are allowed to adsorb by a porous resin and the chlorogenic acid alone is recovered in an elution step, and thus, the adsorption amount of chlorogenic acids is low.

Accordingly, the present invention is to provide a method for producing a purified chlorogenic acids composition having a reduced caffeine content and excellent in taste and flavor, capable of efficiently recovering high purity of chlorogenic acids from a chlorogenic acids-containing composition.

Then, the present inventors investigated on a method for producing a purified chlorogenic acids composition based on the removal rate of caffeine, the yield and purity of a chlorogenic acids composition, and taste and flavor of the resultant chlorogenic acids composition as indicators. As a result, they found that a purified chlorogenic acids composition can be produced in high yield by bringing a chlorogenic acids-containing composition into contact with a cation exchange resin, bringing the treated resultant liquid into contact with an anion exchange resin and subsequently bringing an eluent into contact with the anion exchange resin, and that, in the resultant purified chlorogenic acids composition, the content of caffeine is reduced, purity is high, and taste and flavor thereof are satisfactory. Based on the findings, the present invention was accomplished.

According to the present invention, a high purity of purified chlorogenic acids can be efficiently recovered from a chlorogenic acids-containing composition to obtain a chlorogenic acids composition having good taste and flavor and reduced in caffeine content. The obtained purified chlorogenic acids composition comprises chlorogenic acids at a high concentration and has good taste and flavor. Thus, the composition is useful as food and drink including a beverage.

The method for producing a purified chlorogenic acids-containing composition of the present invention comprises the step A, the step B and the step C as mentioned above. Now, individual steps will be more specifically described, below.

(Step A)

According to the present invention, the step A is a step of bringing a chlorogenic acids-containing composition into contact with a cation exchange resin.

Herein, the "chlorogenic acids" used in the present specification is a generic term which collectively refers to monocaffeoylquinic acids including 3-caffeoylquinic acid, 4-caffeoylquinic acid and 5-caffeoylquinic acid; monoferuloylquinic acids including 3-feruloylquinic acid, 4-feruloylquinic acid and 5-feruloylquinic acid; and dicaffeoylquinic acids including 3,4-dicaffeoylquinic acid, 3,5-dicaffeoylquinic acid and 4,5-dicaffeoylquinic acid. The content of chlorogenic acids is defined based on the total amount of nine chlorogenic acids mentioned above.

The chlorogenic acids-containing composition used as a starting material is not particularly limited as long as it contains chlorogenic acids. A plant extract containing chlorogenic acids may be used. Examples of such a plant extract include coffee beans, sunflower seeds, unripe apples, Simon leaves, cones of the pine family and seed husk of the pine family. Of them, since the content of chlorogenic acids is high, a coffee bean extract is preferable. Note that an extraction method and extraction conditions are not particularly limited.

The coffee beans used as the starting material may be either green beans or roasted beans. The L value of coffee beans is from 20 to 100, preferably from 25 to 95, more preferably from 35 to 90, and even more preferably from 50 to 80, in view of the content of chlorogenic acids.

In the case where a coffee bean extract is used as the chlorogenic acids-containing composition used as the starting material, water, a water miscible organic solvent and a mixture of these can be used as an extraction solvent. The obtained extract solution may be diluted or concentrated and put in use. Furthermore, as the chlorogenic acids-containing composition used as the starting material, a liquid prepared by removing a solvent from the obtained extract solution to obtain a dried product and dissolving the dried product again in a solvent, may be used. More specifically, an extract solution of roasted coffee beans or green coffee beans with water or a mixture of water-water miscible organic solvent, a mixture of these extract solutions or a diluted extract solution, a concentrated extract solution or the like is preferably used.

The water miscible organic solvent to be used in extraction of coffee beans refers to an organic solvent miscible with water in an arbitrary ratio. Examples thereof include ethanol, methanol, isopropyl alcohol, acetone, acetonitrile and a mixture of two or more solvents. Of them, an alcohol such as ethanol, methanol and isopropyl alcohol, and a mixture of two or more solvents are preferable in view of an extraction ratio and particularly ethanol is preferable in consideration of usage in food.

Furthermore, when a mixture of a water miscible organic solvent and water is used, the mass ratio of the water miscible organic solvent/water is preferably smaller than 70/30. In extraction, an organic acid or an organic acid salt such as sodium ascorbate may be added to water or a mixture of water and a water miscible organic solvent or the like in advance.

The extraction temperature is preferably 50° C. or larger, more preferably 80° C. or larger, and also preferably 180° C. or smaller, more preferably 150° C. or smaller, even more preferably 100° C. or smaller, in view of extraction efficiency.

Examples of an extraction method include a method (batch method) in which coffee beans are added to e.g., water or a mixture of a water miscible organic solvent and water and heated while stirring to obtain an extract solution, and a method (column method) in which e.g., water or a mixture of a water miscible organic solvent and water is passed through a column packed with coffee beans at normal temperature or high temperature, under normal pressure or elevated pressure conditions to allow an extraction, and the like. Furthermore, an extraction method performed under so-called non-oxidative atmosphere while removing air by boiling or removing dissolved oxygen by supplying an inert gas such as nitrogen gas, may be used in combination.

The content of chlorogenic acids in a chlorogenic acids-containing composition used as the starting material is not particularly limited; however, the content of chlorogenic acids in an aqueous solution of the chlorogenic acids-containing composition when bringing it into contact with a cation exchange resin is preferably 0.1 mass % or larger, more preferably 0.5 mass % or larger, and even more preferably 1 mass % or larger. The content of chlorogenic acids is preferably 20 mass % or smaller, more preferably 10 mass % or smaller and even more preferably 5 mass % or smaller. A specific content of chlorogenic acids is preferably from 0.1 to 20 mass %, more preferably from 0.5 to 20 mass %, more preferably from 0.5 to 10 mass % and even more preferably from 1 to 5 mass %.

As the cation exchange resin used in the step A, either a strongly acidic cation exchange resin or a weakly acidic cation exchange resin can be used. A resin base, a resin structure and a functional group are not particularly limited; however, as a resin base, for example, a styrene-based resin such as styrene-divinylbenzene, acrylic-based and methacrylic-based resins are mentioned. As the resin structure, for example, a gel type and a porous type are mentioned. The gel type herein refers to a resin having only fine pores (micro pores) formed by swelling; whereas the porous type refers to a resin having macro pores, which are fine pores physically formed and never disappear even in dry conditions, other than micro pores. Specific examples of the strongly acidic cation exchange resin include DIAION SK1B, SK1BH, SK102, SK116, PK208, PK212 (manufactured by Mitsubishi Chemical Corporation), AMBERLITE 200CT, IR118, IR120B, IR124 (manufactured by Dow Chemical Company), and the like. Examples of the functional group of a strongly acidic cation exchange resin include a sulfonic acid group, and the like. Specific examples of the weakly acidic cation exchange resin include DIAION WK10, WK40L (manufactured by Mitsubishi Chemical Corporation), AMBERLITE IRC76 (manufactured by Dow Chemical Company), and the like. Examples of the functional group of a weakly acidic cation exchange resin include a carboxylic acid group, and the like.

As the cation exchange resin used in this step, a proton type cation exchange resin is preferably used in view of removability of impurities. Examples of the proton type cation exchange resin include a cation exchange resin prepared by substituting a $Na^+$ cation exchange resin with $H^+$. Specifically, SK1BH is mentioned.

Furthermore, it is preferable that a cation exchange resin is previously washed with water to remove a starting monomer in the cation exchange resin and impurities in the starting monomer. As a washing condition, for example, a space velocity (SV)=from 1 to 20 $[hr^{-1}]$ is preferably employed and water is preferably used in an amount of from 1 to 100 mass part relative to a cation exchange resin (1 mass part).

A system of bringing a chlorogenic acids-containing composition into contact with a cation exchange resin may be a batch system or a column system; however, a column system is preferable in view of working efficiency. In the column system, a solution containing a chlorogenic acids-containing composition may be passed through a column packed with a cation exchange resin.

As a condition in which a chlorogenic acids-containing composition is brought into contact with a cation exchange resin, a space velocity (SV) is preferably 0.1 $[hr^{-1}]$ or larger, more preferably 0.2 $[hr^{-1}]$ or larger, and even more preferably 0.5 $[hr^{-1}]$ or larger. The space velocity is also preferably 50 $[hr^{-1}]$ or smaller, more preferably 10 $[hr^{-1}]$ or smaller, more preferably 8 $[hr^{-1}]$ or smaller and even more preferably 5 $[hr^{-1}]$ or smaller. More specifically, the space velocity is preferably from 0.1 to 50 $[hr^{-1}]$, more preferably from 0.1 to 10 $[hr^{-1}]$, more preferably from 0.2 to 8 $[hr^{-1}]$ and even more preferably from 0.5 to 5 $[hr^{-1}]$.

Furthermore, an aqueous solution dissolving a chlorogenic acids-containing composition is brought into contact with a cation exchange resin (1 mass part) in an amount of preferably 0.5 mass part or larger, more preferably 1 mass part or larger, more preferably 5 mass part or larger, and even more preferably 10 mass part or larger. The aqueous solution to be in contact with cation exchange resin (1 mass part) is preferably 240 mass part or smaller, more preferably 60 mass part or smaller, more preferably 45 mass part or smaller, and even more preferably 40 mass part or smaller. More specifically, the aqueous solution to be in contact with the cation exchange resin (1 mass part) is preferably from 0.5 to 240 mass part, more preferably from 1 to 60 mass part, more preferably from 5 to 45 mass part, and even more preferably from 10 to 40 mass part.

Furthermore, the step A may be performed simultaneously with an extraction of chlorogenic acids-containing composition as a starting material. In other words, the extraction may be performed in the mixed state of coffee beans and a cation exchange resin.

The pH of the liquid obtained in the step A is preferably smaller than 4, more preferably 3.5 or smaller and even more preferably 3 or smaller in view of reduction in caffeine content, and yield, purity and taste and flavor of a chlorogenic acids composition. Furthermore, the pH of the liquid is preferably 0.5 or larger and more preferably 1 or larger. The pH of the liquid is more preferably from 0.5 to 3.5 and even more preferably from 1 to 3. The liquid obtained in the step A herein refers to the liquid obtained after having a chlorogenic acids-containing composition in contact with a cation exchange resin in a batch system and, in the case of a column system, refers to the liquid obtained by passing a solution of a chlorogenic acids-containing composition through a column packed with a cation exchange resin.

(Step B)

According to the present invention, the step B is a step of bringing the liquid obtained in the step A into contact with an anion exchange resin.

As the anion exchange resin used in the step B, a strongly basic anion exchange resin or a weakly basic anion exchange resin may be used. A resin base, a resin structure and a functional group are not particularly limited; however, as a resin base, for example, a styrene-based resin such as styrene-divinylbenzene, acrylic-based and methacrylic-based resins are mentioned. As the resin structure, for example, a gel type and a porous type are mentioned. Specific examples of the strongly basic anion exchange resin include DIAION SA10A, SA20A, PA300, PA400, HPA25 (manufactured by Mitsubishi Chemical Corporation), AMBERLITE IRA400J, IRA400T, IRA402J, IRA402BL, IRA404J, IRA458RF, IRA410J, IRA411, IRA478RF, IRA900, IRA904, IRA910CT, IRA958 (manufactured by Dow Chemical Company), and the like. Specific examples of the functional group of the strongly basic anion exchange resin include a quaternary ammonium group, and the like. Specific examples of the weakly basic anion exchange resin include DIAION WA10, WA20, WA21J, WA30 (manufactured by Mitsubishi Chemical Corporation), AMBERLITE IRA67, IRA743, IRA96SB, XE583, XT6050RF (manufactured by Dow Chemical Company), and the like. Specific examples of the functional group of the weakly basic anion exchange resin include a primary amino group, a secondary amino group, a tertiary amino group, and the like.

Furthermore, it is preferable that an anion exchange resin is previously washed with water to remove a starting monomer in the adsorbent and impurities in the starting monomer. As a washing condition, for example, a space velocity (SV)=from 1 to 20 [hr$^{-1}$] is preferably employed and water is preferably used in an amount of from 1 to 100 mass part relative to an anion exchange resin (1 mass part).

The liquid obtained in the step A may be brought into contact with an anion exchange resin by a batch system or a column system. In view of working efficiency, a column system is preferable. In the case of the column system, it is sufficient that the liquid obtained in the step A is passed through a column packed with an anion exchange resin.

Furthermore, the step A and the step B may be performed at the same time. In other words, a mixture of a cation exchange resin and an anion exchange resin may be brought into contact with a chlorogenic acids-containing composition.

Furthermore, the step A and the step B may be continuously performed. To describe more specifically, the liquid obtained in a column treatment in the step A, without the liquid being homogenized, may be continuously subjected to a column treatment of the step B.

Furthermore, the extraction operation of a starting material, the step A and the step B continuously may be performed. To describe more specifically, a liquid obtained by passing a solvent through a column packed with coffee beans to allow an extraction may be collected and directly and continuously brought into contact with a cation exchange resin and an anion exchange resin without the liquid being homogenized.

As a condition in which the liquid is brought into contact with an anion exchange resin, a space velocity (SV) is preferably 0.1 [hr$^{-1}$] or larger, more preferably 0.2 [hr$^{-1}$] or larger, and even more preferably 0.5 [hr$^{-1}$]. The space velocity is preferably 50 [hr$^{-1}$] or smaller, more preferably 10 [hr$^{-1}$] or smaller, more preferably 8 [hr$^{-1}$] or smaller, and even more preferably 5 [hr$^{-1}$] or smaller. More specifically, the space velocity is preferably from 0.1 to 50 [hr$^{-1}$], more preferably from 0.1 to 10 [hr$^{-1}$], more preferably from 0.2 to 8 [hr$^{-1}$] and even more preferably from 0.5 to 5 [hr$^{-1}$].

Furthermore, the amount of the liquid obtained in the step A to be passed through a column is not limited as long as the total amount of chlorogenic acids can be adsorbed. The liquid obtained in the step A is passed through an anion exchange resin in a flow ratio of preferably 1 [mL/mL] or larger, more preferably 2 [mL/mL] or larger, and even more preferably 5 [mL/mL] or larger; and preferably 240 [mL/mL] or smaller, more preferably 30 [mL/mL] or smaller, more preferably 25 [mL/mL] or smaller, and even more preferably 20 [mL/mL] or smaller. More specifically, the flow ratio is preferably from 1 to 240 [mL/mL], more preferably from 1 to 30 [mL/mL], more preferably from 2 to 25 [mL/mL], and even more preferably from 5 to 20 [mL/mL].

Furthermore, the amount of the aqueous solution dissolving a chlorogenic acids-containing composition obtained in the step A and to be passed through a column is not limited as long as the total amount of chlorogenic acids can be adsorbed. The aqueous solution dissolving a chlorogenic acids-containing composition obtained in the step A is brought in contact with the anion exchange resin (1 mass part) in an amount of preferably 1 mass part or larger, more preferably 2 mass part or larger, and even more preferably 5 mass part or larger. Furthermore, the aqueous solution to be in contact with an anion exchange resin (1 mass part) is preferably 240 mass part or smaller, 30 mass part or smaller, more preferably 25 mass part or smaller, and even more preferably 20 mass part or smaller. Specifically, the aqueous solution to be in contact with an anion exchange resin (1 mass part) is preferably from 1 to 240 mass part, more preferably from 1 to 30 mass part, more preferably from 2 to 25 mass part, and even more preferably from 5 to 20 mass part.

Note that, after the step B, the anion exchange resin is preferably washed with water before subjected to the step C (described later) in view of purity-improvement of chlorogenic acids and removal of foreign taste from a chlorogenic acids composition.

As a washing condition with water, it is preferable to pass water through a column at a space velocity (SV) of preferably 0.1 [hr$^{-1}$] or larger and even preferably 0.2 [hr$^{-1}$] or larger, and preferably 10 [hr$^{-1}$] or smaller and more preferably 5 [hr$^{-1}$] or smaller. Specifically, water is passed through a column at a space velocity of from 0.1 to 10 [hr$^{-1}$], and more preferably from 0.2 to 5 [hr$^{-1}$]. Furthermore, the amount of water to be passed through a column is preferably 1 mass part or larger, 30 mass part or smaller and more preferably 15 mass part or smaller relative to an anion exchange resin (1 mass part). More specifically, the amount of water relative to an anion exchange resin (1 mass part) is preferably from 1 to 30 mass part and more preferably from 1 to 15 mass part.

(Step C)

According to the present invention, the step C is a step of bringing an eluent into contact with the anion exchange resin after the step B.

As the eluent used in the step C, one or more solutions selected from the group consisting of aqueous alkali hydroxide solutions such as an aqueous sodium hydroxide solution and an aqueous potassium hydroxide solution, and aqueous alkali carbonate solutions such as an aqueous sodium carbonate solution and an aqueous potassium carbonate solution may be used alone or as a mixture.

As the eluent used in this step, an aqueous sodium hydroxide solution is preferable in view of yield of chlorogenic acids.

The concentration of an aqueous alkaline solution is preferably 0.01 mass % or larger, more preferably 0.08 mass % or larger, and even more preferably 0.1 mass % or larger in view of yield of chlorogenic acids; and preferably 10 mass % or smaller, more preferably 1.0 mass % or smaller, more preferably 0.8 mass % or smaller, and even more preferably 0.5 mass % or smaller. Specifically, the concentration is preferably from 0.01 to 10 mass %, more preferably from 0.01 to 1.0 mass %, more preferably from 0.08 to 0.8 mass % and even more preferably from 0.1 to 0.5 mass % in view of yield and purity of chlorogenic acids.

As a condition in which an eluent is brought into contact with an anion exchange resin, a space velocity (SV) is preferably 1 [hr$^{-1}$] or larger, more preferably 2 [hr$^{-1}$] or larger, and even more preferably 3 [hr$^{-1}$] or larger. The space velocity is preferably 50 [hr$^{-1}$] or smaller, more preferably 20 [hr$^{-1}$] or smaller, more preferably 15 [hr$^{-1}$] or smaller, and even more preferably 10 [hr$^{-1}$] or smaller. Specifically, a space velocity is preferably from 1 to 50 [hr$^{-1}$], more preferably from 1 to 20 [hr$^{-1}$], more preferably from 2 to 15 [hr$^{-1}$] and even more preferably from 3 to 10 [hr$^{-1}$].

Furthermore, the eluent is preferably brought into contact with an anion exchange resin (1 mass part) in an amount of preferably 1 mass part or larger, more preferably 10 mass part or larger, more preferably 15 mass part or larger, and even more preferably 20 mass part or larger. Furthermore, the eluent to be in contact with an anion exchange resin (1 mass part) is preferably 100 mass part or smaller, more preferably 50 mass part or smaller, more preferably 45 mass part or smaller, and even more preferably 40 mass part or smaller. Specifically, the eluent to be contact with an anion exchange resin (1 mass part) is preferably from 1 to 100 mass part, more preferably from 10 to 50 mass part, more preferably from 15 to 45 mass part, and even more preferably from 20 to 40 mass part.

A purified chlorogenic acids composition of the present invention can be obtained as an eluent containing chlorogenic acids, by the step C.

pH of the purified chlorogenic acids composition obtained by the step C may be adjusted in view of stability of the chlorogenic acids composition. As a method for adjusting pH, adjustment with an acid, removal of alkaline metal ions byelectrodialysis, or removal of alkaline metal ions by an ion exchange resin may be used. For convenience sake in view of a process, pH is preferably adjusted by a cation exchange resin. As the cation exchange resin, the same cation exchange resin as used in the step A can be used. Note that, pH after pH adjustment is preferably 2 or larger and preferably 7 or smaller, more preferably 5 or smaller, and even more preferably 4 or smaller. Specifically, pH is preferably from 2 to 7, more preferably from 2 to 5 and even more preferably from 2 to 4.

The purified chlorogenic acids composition obtained by the step C can be further treated with activated carbon to reduce foreign taste and foreign odor derived from coffee beans and impurities. The activated carbon to be used is not particularly limited as long as it can be industrially used. Examples thereof that can be used include commercially available products such as ZN-50, Y-10S, GS-1, GS-B (manufactured by Ajinomoto Fine-Techno Co., Inc.); KURARAY COAL GLC, KURARAY COAL PK-D, KURARAY COAL PW-D, KURARAY COAL GW, KURARAY COAL GA, KURARAY COAL GA-D, KURARAY COAL RP-15 (manufactured by KURARAY CHEMICAL CO., LTD.); SHIRASAGI AW50, SHIRASAGI A, SHIRASAGI P, SHIRASAGI KL, SHIRASAGI M, SHIRASAGI C, Carborafin, WH2C (manufactured by Japan EnviroChemicals. Ltd.); GM130A, CW130A, CW130AR, CW350AR, GL130A, SG, SGA, SGP (manufactured by FUTAMURA CHEMICAL CO., LTD.); Yashicoal, MAS jirusi, Umehachi jirusi, Umehachi F jirusi (manufactured by Taihei Chemical Industrial Co., Ltd.); and CPG, CAL, S80A (manufactured by Mitsubishi Chemical Calgon).

In view of improving color of a product, reducing the use amount of activated carbon and improving yield, the activated carbons satisfying the following conditions are preferable. The pore diameter is preferably from 50 to 1000 nm (nanometers), more preferably from 100 to 900 nm (nanometers), and even more preferably from 200 to 800 nm (nanometers). The pore volume is preferably from 0.01 to 2 mL/g, more preferably from 0.1 to 1.5 mL/g, and even more preferably from 0.5 to 1.2 mL/g. Furthermore, the specific surface area falls within the range of preferably from 800 to 2000 m$^2$/g, more preferably from 900 to 1600 m$^2$/g, and even more preferably from 1000 to 1500 m$^2$/g. Note that the values of these physical properties are based on values obtained by a nitrogen adsorption method.

The purified chlorogenic acids composition obtained by the present invention has a feature in that the contents of protein and citric acid relative to chlorogenic acids fall within predetermined ranges. Owing to such a feature, the purified chlorogenic acids composition of the present invention has good taste and flavor and is useful as food and drink such as a beverage.

More specifically, in the purified chlorogenic acids composition obtained by the present invention, the ratio (mass ratio) of protein/chlorogenic acids is 0.1 or smaller, and the ratio (mass ratio) of citric acid/chlorogenic acids is 0.05 or larger and the content of chlorogenic acids in solids is 60 mass % or larger.

The range of the ratio of protein/chlorogenic acids is preferably 0.1 or smaller, and more preferably 0.05 or smaller. The ratio of protein/chlorogenic acids is preferably 0 or larger, and more preferably 0.01 or larger. Furthermore, the range of the ratio of citric acid/chlorogenic acids is preferably 0.05 or larger and more preferably 0.1 or larger. If the ratio of protein/chlorogenic acids and the ratio of citric acid/chlorogenic acids fall within the above ranges, particularly good taste and flavor are obtained. The ratio of citric acid/chlorogenic acids is preferably 0.5 or smaller, more preferably 0.3 or smaller, and even more preferably 0.2 or smaller.

Furthermore, in the purified chlorogenic acids composition obtained by the present invention, the ratio of sucrose/chlorogenic acids is preferably 0.4 or smaller, more preferably 0.1 or smaller and even more preferably 0.01 or smaller. The lower limit of the ratio of sucrose/chlorogenic acids is preferably 0.

Furthermore, in the purified chlorogenic acids composition obtained by the present invention, the ratio (mass ratio) of malic acid/chlorogenic acids is preferably 0.02 or larger, more preferably 0.025 or larger and even more preferably 0.03 or larger. The ratio of malic acid/chlorogenic acids is preferably 0.3 or smaller, more preferably 0.2 or smaller, and even more preferably 0.1 or smaller.

Furthermore, in the purified chlorogenic acids-containing composition obtained by the present invention, the content of chlorogenic acids in solids is preferably 60 mass % or larger, more preferably from 60 to 90 mass %, more preferably from 60 to 85 mass % and even more preferably from 60 to 80 mass %.

Furthermore, in the purified chlorogenic acids composition obtained by the present invention, the ratio (mass ratio) of caffeine/chlorogenic acids is 0.04 or smaller and preferably 0.035 or smaller. The lower limit of the ratio of caffeine/chlorogenic acids is preferably 0.

Next, embodiments and exemplified embodiments of the present invention will be described below.

<1> A method for producing a purified chlorogenic acids composition, comprising
a step A of bringing a chlorogenic acids-containing composition into contact with a cation exchange resin;
a step B of bringing the liquid obtained in the step A into contact with an anion exchange resin; and
a step C of bringing an eluent into contact with the anion exchange resin after the step B.

<2> The producing method according to <1>, in which the content of chlorogenic acids in a starting chlorogenic acids-containing composition is 0.1 mass % or larger, preferably 0.5 mass % or larger, and more preferably 1 mass % or larger, and 20 mass % or smaller, preferably 10 mass % or smaller, and more preferably 5 mass % or smaller.

<3> The producing method according to <1> or <2>, in which the starting chlorogenic acids-containing composition is an extract of coffee bean.

<4> The producing method according to <1> to <3>, in which the cation exchange resin of the step A is a proton-type cation exchange resin.

<5> The producing method according to <1> to <4>, in which, in the step A, as a condition in which the chlorogenic acids-containing composition is brought into contact with the cation exchange resin, a space velocity (SV) is 0.1 [hr$^{-1}$] or larger, preferably 0.2 [hr$^{-1}$] or larger and more preferably 0.5 [hr$^{-1}$] or larger; 50 [hr$^{-1}$] or smaller, preferably 10 [hr$^{-1}$] or smaller, more preferably 8 [hr$^{-1}$] or smaller, and even more preferably 5 [hr$^{-1}$] or smaller; and more preferably from 0.1 to 50 [hr$^{-1}$], more preferably from 0.1 to 10 [hr$^{-1}$], more preferably from 0.2 to 8 [hr$^{-1}$], and even more preferably from 0.5 to 5 [hr$^{-1}$].

<6> The producing method according to <1> to <5>, in which, in the step A, an aqueous solution dissolving the chlorogenic acids-containing composition is brought into contact with a cation exchange resin (1 mass part) in an amount of 0.5 mass part or larger, preferably 1 mass part or larger, more preferably 5 mass part or larger, and even more preferably 10 mass part or larger; 240 mass part or smaller, preferably 60 mass part or smaller, more preferably 45 mass part or smaller, and even more preferably 40 mass part or smaller; and more preferably from 0.5 to 240 mass part, more preferably from 1 to 60 mass part, more preferably from 5 to 45 mass part, and even more preferably from 10 to 40 mass part.

<7> The producing method according to <1> to <6>, in which the pH of the liquid obtained in the step A is smaller than 4, preferably 3.5 or smaller and more preferably 3 or smaller; 0.5 or larger and preferably 1 or larger; and more preferably from 0.5 to 3.5 and even more preferably from 1 to 3.

<8> The producing method according to <1> to <7>, in which the anion exchange resin used in the step B is a weakly basic anion exchange resin.

<9> The producing method according to <1> to <8>, in which, as a condition in which the liquid is brought into contact with an anion exchange resin in the step B, a space velocity (SV) is 0.1 [hr$^{-1}$] or larger, preferably 0.2 [hr$^{-1}$] or larger and more preferably 0.5 [hr$^{-1}$] or larger; 50 [hr$^{-1}$] or smaller, preferably 10 [hr$^{-1}$] or smaller, more preferably 8 [hr$^{-1}$] or smaller and even more preferably 5 [hr$^{-1}$] or smaller; and more preferably from 0.1 to 50 [hr$^{-1}$], more preferably from 0.1 to 10 [hr$^{-1}$], more preferably from 0.2 to 8 [hr$^{-1}$] and even more preferably from 0.5 to 5 [hr$^{-1}$].

<10> The producing method according to <1> to <9>, in which, the liquid obtained in the step A is passed through an anion exchange resin in a flow ratio of 1 [mL/mL] or larger, preferably 2 [mL/mL] or larger, and more preferably 5 [mL/mL] or larger; 240 [mL/mL] or smaller, preferably 30 [mL/mL] or smaller, more preferably 25 [mL/mL] or smaller and even more preferably 20 [mL/mL] or smaller; and more preferably from 1 to 240 [mL/mL], more preferably from 1 to 30 [mL/mL], more preferably from 2 to 25 [mL/mL] and even more preferably from 5 to 20 [mL/mL].

<11> The producing method according to <1> to <10>, in which in the step B, an aqueous solution dissolving a chlorogenic acids-containing composition is brought into contact with the anion exchange resin (1 mass part) in an amount of 1 mass part or larger, preferably 2 mass part or larger, and more preferably 5 mass part or larger; 240 mass part or smaller, preferably 30 mass part or smaller, more preferably 25 mass part or smaller, and even more preferably 20 mass part or smaller; and more preferably from 1 to 240 mass part, more preferably from 1 to 30 mass part, more preferably from 2 to 25 mass part and even more preferably from 5 to 20 mass part.

<12> The producing method according to <1> to <11>, in which the liquid obtained in the step A is brought into contact with the anion exchange resin, and then (between the step B and the step C) the anion exchange resin is washed with water.

<13> The producing method according to <12>, in which as a washing condition with water, the amount of water to be passed through an anion exchange resin (1 mass part) is 1 mass part or larger, 30 mass part or smaller and preferably 15 mass part or smaller, more preferably 1 to 30 mass part, and even more preferably from 1 to 15 mass part at a space velocity (SV) of 0.1 [hr$^{-1}$] or larger, and preferably 0.2 [hr$^{-1}$] or larger; 10 [hr$^{-1}$] or smaller and preferably 5 [hr$^{-1}$] or smaller; more preferably from 0.1 to 10 [hr$^{-1}$], and even more preferably from 0.2 to 5 [hr–1].

<14> The producing method according to <1> to <13>, in which the eluent used in the step C is an aqueous alkaline solution selected from an aqueous alkali hydroxide solution and an aqueous alkali carbonate solution, and is preferably an aqueous sodium hydroxide solution.

<15> The producing method according to <14>, in which the concentration of the aqueous alkaline solution used in the step C is 0.01 mass % or larger, preferably 0.08 mass % or larger, and more preferably 0.1 mass % or larger; 10 mass % or smaller, preferably 1.0 mass % or smaller, more preferably 0.8 mass % or smaller, and even more preferably 0.5 mass % or smaller; and more preferably from 0.01 to 10 mass %, more preferably from 0.01 to 1.0 mass %, more preferably from 0.08 to 0.8 mass %, and even more preferably from 0.1 to 0.5 mass %.

<16> The producing method according to <1> to <15>, in which, in the step C, as a condition in which an eluent is brought into contact with the anion exchange resin, a space velocity (SV) is 1 [$hr^{-1}$] or larger, preferably 2 [$hr^{-1}$] or larger, and more preferably 3 [$hr^{-1}$] or larger; 50 [$hr^{-1}$] or smaller, preferably 20 [$hr^{-1}$] or smaller, more preferably 15 [$hr^{-1}$] or smaller, and even more preferably 10 [$hr^{-1}$] or smaller; and more preferably from 1 to 50 [$hr^{-1}$], more preferably from 1 to 20 [$hr^{-1}$], more preferably from 2 to 15 [$hr^{-1}$] and even more preferably from 3 to 10 [$hr^{-1}$].

<17> The producing method according to <1> to <16>, in which, in the step C, the eluent is brought into contact with the anion exchange resin (1 mass part) in an amount of 1 mass part or larger, preferably 10 mass part or larger, more preferably 15 mass part or larger, and even more preferably 20 mass part or larger; 100 mass part or smaller, preferably 50 mass part or smaller, more preferably 45 mass part or smaller, and even more preferably 40 mass part or smaller; and more preferably from 1 to 100 mass part, more preferably from 10 to 50 mass part, more preferably from 15 to 45 mass part, and even more preferably from 20 to 40 mass part.

<18> The producing method according to <1> to <17>, in which, after the step C, pH of the purified chlorogenic acids composition is adjusted to 2 or larger and 7 or smaller, preferably 5 or smaller, and more preferably 4 or smaller; and more preferably from 2 to 7, more preferably from 2 to 5 and even more preferably from 2 to 4.

<19> The producing method according to <1> to <18>, in which, after the step C, the purified chlorogenic acids composition is further treated with activated carbon.

<20> A purified chlorogenic acids composition, in which the ratio of protein/chlorogenic acids is 0.1 or smaller, the ratio of citric acid/chlorogenic acids is 0.05 or larger, and the content of chlorogenic acids in solids is 60 mass % or larger.

<21> The composition according to <20>, in which the ratio of protein/chlorogenic acids is 0.1 or smaller and preferably 0.05 or smaller; and 0 or larger, and preferably 0.01 or larger.

<22> The composition according to <20> or <21>, in which the ratio of citric acid/chlorogenic acids is 0.05 or larger and preferably 0.1 or larger; and 0.5 or smaller, preferably 0.3 or smaller and more preferably 0.2 or smaller.

<23> The composition according to <20> to <22>, in which the ratio of sucrose/chlorogenic acids is 0.4 or smaller, preferably 0.1 or smaller, and more preferably 0.01 or smaller.

<24> The composition according to <20> to <23>, in which the ratio of malic acid/chlorogenic acids is 0.02 or larger, preferably 0.025 or larger, and more preferably 0.03 or larger; and 0.3 or smaller, preferably 0.2 or smaller, and more preferably 0.1 or smaller.

<25> The composition according to <21> to <24>, in which the content of chlorogenic acids in solids of the purified chlorogenic acids-containing composition is 60 mass % or larger, preferably from 60 to 90 mass %, more preferably from 60 to 85 mass %, and even more preferably from 60 to 80 mass %.

<26> The composition according to <21> to <25>, in which the ratio of caffeine/chlorogenic acids is 0.04 or smaller, and preferably 0.03 or smaller.

EXAMPLES

Evaluation Method 1

(1) Evaluation of taste and flavor (coarseness)

Each of the chlorogenic acids compositions obtained in Examples and Comparative Examples was diluted with distillation water such that chlorogenic acids were contained in a concentration of 0.6 mass %. A panel of five experts took the diluted composition and sensuously evaluated it based on the following standards. Note that, the average evaluation results are shown in Table 1. The term "coarseness" herein refers to e.g., bitterness and astringency.

(Evaluation Standards)

4: Coarseness is considerably slightly sensed

3: Coarseness is slightly sensed

2: Coarseness is sensed

1: Coarseness is considerably sensed (2) Evaluation of Taste and Flavor (Fresh Sourness)

Each of the chlorogenic acids compositions obtained in Examples and Comparative Examples was diluted with distillation water such that chlorogenic acids were contained in a concentration of 0.6 mass %. A panel of five experts took the diluted composition and sensuously evaluated it based on the following standards. Note that, the average evaluation results are shown in Table 1. The term "fresh sourness" herein refers to pure sourness without astringent taste and stimulus giving tongue numbness.

(Evaluation Standards)

4: Fresh sourness is considerably sensed

3: Fresh sourness is sensed

2: Fresh sourness is slightly sensed

1: Fresh sourness is considerably slightly sensed (3) Method for Measuring Chlorogenic Acids and Caffeine (Analyzer)

HPLC (manufactured by Hitachi, Ltd.) was used. The followings are the model numbers of component units in the analyzer.

Pump unit (with a built-in degasser): L-2130,

Autosampler (equipped with cooler): L-2200,

Column oven: L-2300,

Separation column: Cadenza CD-C18, Size: 4.6 mm i.d.× 150 mm, 3 µm (Intact Corp.)

Detector (UV-visible spectrophotometer): L-2420

(Analysis Conditions)

Sample injection amount: 10 µL,

Flow rate: 1.0 mL/min,

Detection wavelength by the UV absorptiometer: 325 nm (for chlorogenic acids), 270 nm (for caffeine), Eluent A: 5% acetonitrile containing 0.05 mol/L acetic acid, 0.01 mol/L sodium acetate, and 0.1 mmol/L HEDPO (1-hydroxyethane-1,1-diphosphonic acid)
Eluent B: Acetonitrile

TABLE 1

(Concentration-gradient conditions)

| Time (Minutes) | Eluent A (% (v/v)) | Eluent B (% (v/v)) |
|---|---|---|
| 0 | 100 | 0 |
| 10 | 100 | 0 |
| 15 | 95 | 5 |
| 20 | 95 | 5 |
| 22 | 92 | 8 |
| 50 | 92 | 8 |
| 52 | 10 | 90 |
| 60 | 10 | 90 |
| 60.1 | 100 | 0 |
| 70 | 100 | 0 |

(Retention Time of Chlorogenic Acids)
3-caffeoylquinic acid (3-CQA): 5.2 min,
5-caffeoylquinic acid (5-CQA): 8.7 min,
4-caffeoylquinic acid (4-CQA): 11.2 min,
3-feruloylquinic acid (3-FQA): 12.6 min,
5-feruloylquinic acid (5-FQA): 19.1 min,
4-feruloylquinic acid (4-FQA): 20.9 min,
3,5-dicaffeoylquinic acid (3,5-diCQA): 37.0 min,
3,4-dicaffeoylquinic acid (3,4-diCQA): 37.5 min,
4,5-dicaffeoylquinic acid (4,5-diCQA): 44.8 min From area percentages obtained herein, the amounts of chlorogenic acids were quantitated using 5-CQA as a standard substance.
(Retention Time of Caffeine)
18.8 min
From area percentages obtained herein, the amount of caffeine was quantitated using a reagent caffeine as a standard substance.
(Yield of a Chlorogenic Acids Composition)
The yield of a chlorogenic acids composition was obtained by dividing the amount of chlorogenic acids contained in each of the chlorogenic acids compositions obtained in Examples and Comparative Examples by the amount of chlorogenic acids contained in the starting material chlorogenic acids-containing composition.
(Content Ratio of Caffeine)
The content ratio of caffeine was obtained by dividing the amount of caffeine contained in each of the chlorogenic acids compositions obtained in Examples and Comparative Examples by the total mass of each of the chlorogenic acids compositions obtained in Examples and Comparative Examples.
(Content Ratio of Chlorogenic Acids)
The content ratio of chlorogenic acids was obtained by dividing the amount of chlorogenic acids contained in each of the chlorogenic acids compositions obtained in Examples and Comparative Examples by the total mass of each of the chlorogenic acids compositions obtained in Examples and Comparative Examples.
(Ratio of Caffeine/Chlorogenic Acids)
The ratio of caffeine/chlorogenic acids was obtained by dividing the amount of caffeine contained in each of the chlorogenic acids compositions obtained in Examples and Comparative Examples by the amount of chlorogenic acids contained in each of the chlorogenic acids compositions obtained in Examples and Comparative Examples.

(Purity of Chlorogenic Acids)
The purity of chlorogenic acids was obtained by dividing the mass of chlorogenic acids contained in solids of a chlorogenic acids composition by the mass of the solids of the chlorogenic acids composition.
Herein, the term "solids" in the present specification refers to a residue of a sample from which volatile substances are removed by drying the sample in an electric isothermal dryer at 105° C. for 3 hours.
(Measurement of Protein)
The amount of protein was calculated by multiplying a value obtained by subtracting the amount of nitrogen derived from caffeine from the total amount of nitrogen, by 6.25. The analysis of the total nitrogen amount was commissioned to the Japanese Food Research Laboratories.
(Analysis of Total Nitrogen Amount)
A sample was taken and a decomposition accelerator (copper sulfate:potassium sulfate=1:9) (10 g) and concentrated sulfuric acid (15 mL) were added thereto. After thermolysis was performed for one hour, the resultant mixture was allowed to cool. Subsequently, ion exchange water was added and, a sodium hydroxide solution was added and distilled by application of heat in the presence of excessive alkali. Thereafter, the distillate was titrated with a 0.05 mol/L sulfuric acid standard solution V mL with a bromcresol green/methyl red solution used as an indicator.
The total nitrogen amount was calculated in accordance with the following expression.

$$\text{Total nitrogen}(g/100\ g) = \{[(V-B) \times F \times 0.0014]/S\} \times 100$$

V: Titration value of a test sample (mL)
B: Titration value of blank (mL)
F: Titer of 0.05 mol/L sulfuric acid standard solution 0.0014: the amount (g) of nitrogen relative to 0.05 mol/L of sulfuric acid standard solution (1 mL)
S: Taken amount (g) of a sample
(Organic Acid (Citric Acid, Malic Acid, Quinic Acid))
A sample and a 5% perchloric acid were mixed and then ion exchange water was added up to a predetermined volume. Then, the mixture was diluted, filtered and analyzed by high-speed liquid chromatography.
(Analyzer)
Type: LC-20AD (manufactured by Shimadzu Corporation)
Detector: UV-visible absorptiometer SPD-20AV (manufactured by Shimadzu Corporation)
Column: Gelpack GL-C610H-S×2 φ7.8 mm×300 mm (manufactured by Hitachi Chemical Co., Ltd.)
Column temperature: 40° C.
Mobile phase: 3 mmol/L perchloric acid
Reaction solution: 15 mmol/L disodium hydrogen-phosphate solution containing 0.2 mmol/L bromothymol blue
Flow rate: mobile phase 0.5 mL/min, reaction solution 0.6 mL/min
Measurement wavelength: 445 nm
(Sucrose)
After a sample was neutralized, an extraction was performed by application of ultrasonic wave for 30 minutes. Subsequently, ion exchange water was added up to a predetermined volume, and then, the sample was purified, filtered and analyzed by high-speed liquid chromatography.
(Analyzer)
Type: LC-10ADvp (manufactured by Shimadzu Corporation)
Detector: Differential refractometer RID-10A (manufactured by Shimadzu Corporation)

Column: Shodex Asahipak NH2P-50 4E φ4.6 mm×250 mm (manufactured by SHOWA DENKO K. K.)
Column temperature: Room temperature
Mobile phase: acetonitrile:water=81:19
Flow rate: 1 mL/min
Injection amount: 20 μL Preparation Example 1

*Coffea Robusta* green coffee beans (L value 65) was extracted with hot water and dried to obtain a powdery chlorogenic acids-containing composition, in which the content of chlorogenic acids was 40.8 mass %, the content of caffeine was 9.8 mass %, the content of sucrose was 19.7 mass %, the content of protein was 8.7 mass %, the content of citric acid was 3.9 mass %, the content of malic acid was 1.1 mass %, the content of a quinic acid was 1.2 mass % and the ratio of the caffeine content/chlorogenic acids content was 0.24. The powdery composition was used as a starting material.

The starting material chlorogenic acids-containing composition was dissolved in ion exchange water such that the content of chlorogenic acids was 1.2 mass %. In this manner, "Solution A of the chlorogenic acids-containing composition" was prepared. The pH of the solution was 5.7.

Preparation Example 2

*Coffea Robusta* green coffee beans (L value 65) was extracted with hot water and dried to obtain a powdery chlorogenic acids-containing composition, in which the content of chlorogenic acids was 40.8 mass %, the content of caffeine was 9.8 mass %, the content of sucrose was 19.7 mass %, the content of a protein was 8.7 mass %, the content of citric acid was 3.9 mass %, the content of malic acid was 1.1 mass %, the content of quinic acid was 1.2 mass %, and the ratio of the caffeine content/chlorogenic acids content was 0.24. The powdery composition was used as a starting material.

The starting material chlorogenic acids-containing composition was dissolved in ion exchange water such that the content of chlorogenic acids was 3.6 mass %. In this manner, "Solution B of the chlorogenic acids-containing composition" was prepared. The pH of the solution was 5.6.

Preparation Example 3

*Coffea Robusta* roasted coffee beans (L value 50) was extracted with hot water and dried to obtain a powdery chlorogenic acids-containing composition, in which the content of chlorogenic acids was 34.4 mass %, the content of caffeine was 9.8 mass %, and the ratio of the caffeine content/chlorogenic acids content was 0.28. The powdery composition was used as a starting material.

The starting material chlorogenic acids-containing composition was dissolved in ion exchange water such that the content of chlorogenic acids was 1.2 mass %. In this manner, "Solution C of the chlorogenic acids-containing composition" was prepared. The pH of the solution was 5.5.

Preparation Example 4

*Coffea Robusta* green coffee beans (L value 65) was extracted with hot water to obtain a solution-state chlorogenic acids-containing composition, in which the content of chlorogenic acids was 0.75 mass %, the content of caffeine was 0.18 mass %, and the ratio of the caffeine content/chlorogenic acids content was 0.24. The solution-state composition was used as a starting material and specified as "Solution D of the chlorogenic acids-containing composition". The pH of the solution was 5.6.

Example 1

Solution A obtained in Preparation Example 1 was passed through a column packed with a strongly acidic cation exchange resin (trade name SK1BH, manufactured by Mitsubishi Chemical Corporation) at a flow rate of SV1 [$hr^{-1}$] in an amount of 20 mass part relative to the resin (1 mass part). The pH of the solution after the pass was 2.3.

The solution was passed through a column packed with a weakly basic anion exchange resin (trade name IRA67, manufactured by Dow Chemical Company) at a flow rate of SV1 [$hr^{-1}$] in an amount of 15 mass part relative to the resin (1 mass part). Subsequently, water was passed through the column at a flow rate of SV1 [$hr^{-1}$] in an amount of 2 mass part relative to the resin (1 mass part).

Thereafter, an alkali solution (NaOH: 0.5 mass % solution) was passed through the column at SV5 [$hr^{-1}$] in an amount of 25 mass part relative to the resin (1 mass part). The solution was passed through the column packed with a strongly acidic cation exchange resin (trade name SK1BH, manufactured by Mitsubishi Chemical Corporation) and pH was adjusted to 3.1 to obtain a "purified chlorogenic acids composition". Note that the strongly acidic cation exchange resin used herein was 1.2 mass part relative to the weakly basic anion exchange resin. The "purified chlorogenic acids composition" obtained was evaluated in the conditions described in [Evaluation Method 1].

Example 2

Solution A obtained in Preparation Example 1 was passed through a column packed with a strongly acidic cation exchange resin (trade name SK1BH, manufactured by Mitsubishi Chemical Corporation) at a flow rate of SV1 [$hr^{-1}$] in an amount of 27 mass part relative to the resin (1 mass part). The pH of the solution after the pass was 3.0. The solution was passed through a column packed with a weakly basic anion exchange resin (trade name IRA67, manufactured by Dow Chemical Company) at a flow rate of SV1 [$hr^{-1}$] in an amount of 15 mass part relative to the resin (1 mass part). Subsequently, water was passed through the column at a flow rate of SV1 [$hr^{-1}$] in an amount of 2 mass part relative to the resin (1 mass part).

Thereafter, an alkali solution (NaOH: 0.5 mass % solution) was passed through the column at SV5 [$hr^{-1}$] in an amount of 25 mass part relative to the resin (1 mass part). The solution was passed through the column packed with a strongly acidic cation exchange resin (trade name SK1BH, manufactured by Mitsubishi Chemical Corporation) and pH was adjusted to 3.2 to obtain a "purified chlorogenic acids composition". Note that the strongly acidic cation exchange resin used herein was 1.2 mass part relative to the weakly basic anion exchange resin. The "purified chlorogenic acids composition" obtained was evaluated in the conditions described in [Evaluation Method 1].

Example 3

Solution A obtained in Preparation Example 1 was passed through a column packed with a strongly acidic cation exchange resin (trade name SK1BH, manufactured by Mitsubishi Chemical Corporation) at a flow rate of SV1 [$hr^{-1}$] in an amount of 25 mass part relative to the resin (1 mass part). The pH of the solution after the pass was 2.7.

The solution was passed through a column packed with a weakly basic anion exchange resin (trade name IRA67, manufactured by Dow Chemical Company) at a flow rate of SV1 [hr$^{-1}$] in an amount of 15 mass part relative to the resin (1 mass part). Subsequently, water was passed through the column at a flow rate of SV1 [hr$^{-1}$] in an amount of 2 mass part relative to the resin (1 mass part).

Thereafter, an alkali solution (NaOH: 0.5 mass % solution) was passed through the column at SV5 [hr$^{-1}$] in an amount of 25 mass part relative to the resin (1 mass part). The solution was passed through the column packed with a strongly acidic cation exchange resin (trade name SK1BH, manufactured by Mitsubishi Chemical Corporation) and pH was adjusted to 3.1 to obtain a "purified chlorogenic acids composition". Note that the strongly acidic cation exchange resin used herein was 1.2 mass part relative to the weakly basic anion exchange resin. The "purified chlorogenic acids composition" obtained was evaluated in the conditions described in [Evaluation Method 1].

Example 4

Solution A obtained in Preparation Example 1 was passed through a column packed with a strongly acidic cation exchange resin (trade name SK1BH, manufactured by Mitsubishi Chemical Corporation) at a flow rate of SV1 [hr$^{-1}$] in an amount of 30 mass part relative to the resin (1 mass part). The pH of the solution after the pass was 3.3.

The solution was passed through a column packed with a weakly basic anion exchange resin (trade name IRA67, manufactured by Dow Chemical Company) at a flow rate of SV1 [hr$^{-1}$] in an amount of 15 mass part relative to the resin (1 mass part). Subsequently, water was passed through the column at a flow rate of SV1 [hr$^{-1}$] in an amount of 2 mass part relative to the resin (1 mass part).

Thereafter, an alkali solution (NaOH: 0.5 mass % solution) was passed through the column at SV5 [hr$^{-1}$] in an amount of 25 mass part relative to the resin (1 mass part). The solution was passed through the column packed with a strongly acidic cation exchange resin (trade name SK1BH, manufactured by Mitsubishi Chemical Corporation) and pH was adjusted to 3.2 to obtain a "purified chlorogenic acids composition". Note that the strongly acidic cation exchange resin used herein was 1.2 mass part relative to the weakly basic anion exchange resin. The "purified chlorogenic acids composition" obtained was evaluated in the conditions described in [Evaluation Method 1].

Example 5

Solution A obtained in Preparation Example 1 was passed through a column packed with a strongly acidic cation exchange resin (trade name SK1BH, manufactured by Mitsubishi Chemical Corporation) at a flow rate of SV1 [hr$^{-1}$] in an amount of 20 mass part relative to the resin (1 mass part). The pH of the solution after the pass was 2.3.

The solution was passed through a column packed with a weakly basic anion exchange resin (trade name IRA67 manufactured by Dow Chemical Company) at a flow rate of SV1 [hr$^{-1}$] in an amount of 10 mass part relative to the resin (1 mass part). Subsequently, water was passed through the column at a flow rate of SV1 [hr$^{-1}$] in an amount of 2 mass part relative to the resin (1 mass part).

Thereafter, an alkali solution (NaOH: 0.5 mass % solution) was passed through the column at SV5 [hr$^{-1}$] in an amount of 25 mass part relative to the resin (1 mass part). The solution was passed through the column packed with a strongly acidic cation exchange resin (trade name SK1BH, manufactured by Mitsubishi Chemical Corporation) and pH was adjusted to 3.1 to obtain a "purified chlorogenic acids composition". Note that the strongly acidic cation exchange resin used herein was 1.2 mass part relative to the weakly basic anion exchange resin. The "purified chlorogenic acids composition" obtained was evaluated in the conditions described in [Evaluation Method 1].

Example 6

Solution A obtained in Preparation Example 1 was passed through a column packed with a strongly acidic cation exchange resin (trade name SK1BH, manufactured by Mitsubishi Chemical Corporation) at a flow rate of SV1 [hr$^{-1}$] in an amount of 20 mass part relative to the resin (1 mass part). The pH of the solution after the pass was 2.3.

The solution was passed through a column packed with a weakly basic anion exchange resin (trade name IRA67, manufactured by Dow Chemical Company) at a flow rate of SV1 [hr$^{-1}$] in an amount of 20 mass part relative to the resin (1 mass part). Subsequently, water was passed through the column at a flow rate of SV1 [hr$^{-1}$] in an amount of 2 mass part relative to the resin (1 mass part).

Thereafter, an alkali solution (NaOH: 0.5 mass % solution) was passed through the column at SV5 [hr$^{-1}$] in an amount of 25 mass part relative to the resin (1 mass part). The solution was passed through the column packed with a strongly acidic cation exchange resin (trade name SK1BH, manufactured by Mitsubishi Chemical Corporation) and pH was adjusted to 3.1 to obtain a "purified chlorogenic acids composition". Note that the strongly acidic cation exchange resin used herein was 1.2 mass part relative to the weakly basic anion exchange resin. The "purified chlorogenic acids composition" obtained was evaluated in the conditions described in [Evaluation Method 1].

Example 7

Solution A obtained in Preparation Example 1 was passed through a column packed with a weakly acidic cation exchange resin (trade name WK40L, manufactured by Mitsubishi Chemical Corporation) at a flow rate of SV1 [hr$^{-1}$] in an amount of 20 mass part relative to the resin (1 mass part). The pH of the solution after the pass was 3.3.

The solution was passed through a column packed with a weakly basic anion exchange resin (trade name IRA67, manufactured by Dow Chemical Company) at a flow rate of SV1 [hr$^{-1}$] in an amount of 15 mass part relative to the resin (1 mass part). Subsequently, water was passed through the column at a flow rate of SV1 [hr$^{-1}$] in an amount of 2 mass part relative to the resin (1 mass part).

Thereafter, an alkali solution (NaOH: 0.5 mass % solution) was passed through the column at SV5 [hr$^{-1}$] in an amount of 25 mass part relative to the resin (1 mass part).

The solution was passed through a column packed with a strongly acidic cation exchange resin (trade name SK1BH, manufactured by Mitsubishi Chemical Corporation) and pH was adjusted to 3.1 to obtain a "purified chlorogenic acids composition". Note that the strongly acidic cation exchange resin used herein was 1.2 mass part relative to the weakly basic anion exchange resin. The "purified chlorogenic acids composition" obtained was evaluated in the conditions described in [Evaluation Method 1].

Example 8

Solution B obtained in Preparation Example 2 was passed through a column packed with a strongly acidic cation exchange resin (trade name SK1BH, manufactured by Mitsubishi Chemical Corporation) at a flow rate of SV1 $[hr^{-1}]$ in an amount of 6.8 mass part relative to the resin (1 mass part). The pH of the solution after the pass was 2.0.

The solution was passed through a column packed with a weakly basic anion exchange resin (trade name IRA67, manufactured by Dow Chemical Company) at a flow rate of SV1 $[hr^{-1}]$ in an amount of 5 mass part relative to the resin (1 mass part). Subsequently, water was passed through the column at a flow rate of SV1 $[hr^{-1}]$ in an amount of 2 mass part relative to the resin (1 mass part).

Thereafter, an alkali solution (NaOH: 0.5 mass % solution) was passed through the column at SV5 $[hr^{-1}]$ in an amount of 25 mass part relative to the resin (1 mass part).

The solution was passed through the column packed with a strongly acidic cation exchange resin (trade name SK1BH, manufactured by Mitsubishi Chemical Corporation) and pH was adjusted to 3.1 to obtain a "purified chlorogenic acids composition". Note that the strongly acidic cation exchange resin used herein was 1.2 mass part relative to the weakly basic anion exchange resin. The "purified chlorogenic acids composition" obtained was evaluated in the conditions described in [Evaluation Method 1].

Example 9

Solution C obtained in Preparation Example 3 was passed through a column packed with a strongly acidic cation exchange resin (trade name SK1BH, manufactured by Mitsubishi Chemical Corporation) at a flow rate of SV1 $[hr^{-1}]$ in an amount of 20 mass part relative to the resin (1 mass part). The pH of the solution after the pass was 2.0.

The solution was passed through a column packed with a weakly basic anion exchange resin (trade name IRA67, manufactured by Dow Chemical Company) at a flow rate of SV1 $[hr^{-1}]$ in an amount of 15 mass part relative to the resin (1 mass part). Subsequently, water was passed through the column at a flow rate of SV1 $[hr^{-1}]$ in an amount of 2 mass part relative to the resin (1 mass part).

Thereafter, an alkali solution (NaOH: 0.5 mass % solution) was passed through the column at SV5 $[hr^{-1}]$ in an amount of 25 mass part relative to the resin (1 mass part). The solution was passed through the column packed with a strongly acidic cation exchange resin (trade name SK1BH, manufactured by Mitsubishi Chemical Corporation) and pH was adjusted to 3.0 to obtain a "purified chlorogenic acids composition". Note that the strongly acidic cation exchange resin used herein was 1.2 mass part relative to the weakly basic anion exchange resin. The "purified chlorogenic acids composition" obtained was evaluated in the conditions described in [Evaluation Method 1].

Example 10

Solution D obtained in Preparation Example 4 was passed through a column packed with a strongly acidic cation exchange resin (trade name SK1BH, manufactured by Mitsubishi Chemical Corporation) at a flow rate of SV1.6 $[hr^{-1}]$ in an amount of 32 mass part relative to the resin (1 mass part). The pH of the solution after the pass was 2.4.

The solution was passed through a column packed with a weakly basic anion exchange resin (trade name IRA67, manufactured by Dow Chemical Company) at a flow rate of SV1.6 $[hr^{-1}]$ in an amount of 24 mass part relative to the resin (1 mass part). Subsequently, water was passed through the column at a flow rate of SV1 $[hr^{-1}]$ in an amount of 2 mass part relative to the resin (1 mass part).

Thereafter, an alkali solution (NaOH: 0.5 mass % solution) was passed through the column at SV5 $[hr^{-1}]$ in an amount of 25 mass part relative to the resin (1 mass part). The solution was passed through the column packed with a strongly acidic cation exchange resin (trade name SK1BH, manufactured by Mitsubishi Chemical Corporation) and pH was adjusted to 3.0 to obtain a "purified chlorogenic acids composition". Note that the strongly acidic cation exchange resin used herein was 1.2 mass part relative to the weakly basic anion exchange resin. The "purified chlorogenic acids composition" obtained was evaluated in the conditions described in [Evaluation Method 1].

Comparative Example 1

The solution A obtained in Preparation Example 1 was passed through a column packed with a weakly basic anion exchange resin (trade name IRA67, manufactured by Dow Chemical Company) at a flow rate of SV1 $[hr^{-1}]$ in an amount of 15 mass part relative to the resin (1 mass part). Subsequently, water was passed through the column at a flow rate of SV1 $[hr^{-1}]$ in an amount of 2 mass part relative to the resin (1 mass part).

Thereafter, an alkali solution (NaOH: 0.5 mass % solution) was passed through the column at SV5 $[hr^{-1}]$ in an amount of 25 mass part relative to the resin (1 mass part). The solution was passed through the column packed with a strongly acidic cation exchange resin (trade name SK1BH, manufactured by Mitsubishi Chemical Corporation) and pH was adjusted to 3.1 to obtain a "chlorogenic acids composition". Note that the strongly acidic cation exchange resin used herein was 1.2 mass part relative to the weakly basic anion exchange resin. The "chlorogenic acids composition" obtained was evaluated in the conditions described in [Evaluation Method 1].

Comparative Example 2

To the solution A obtained in Preparation Example 1, hydrochloric acid was added up to pH of 2.3.

The solution was passed through a column packed with a weakly basic anion exchange resin (trade name IRA67, manufactured by Dow Chemical Company) at a flow rate of SV1 $[hr^{-1}]$ in an amount of 15 mass part relative to the resin (1 mass part). Subsequently, water was passed through the column at a flow rate of SV1 $[hr^{-1}]$ in an amount of 2 mass part relative to the resin (1 mass part).

Thereafter, an alkali solution (NaOH: 0.5 mass % solution) was passed through the column at SV5 $[hr^{-1}]$ in an amount of 25 mass part relative to the resin (1 mass part). The solution was passed through the column packed with a strongly acidic cation exchange resin (trade name SK1BH, manufactured by Mitsubishi Chemical Corporation) and pH was adjusted to 3.2 to obtain a "chlorogenic acids composition". Note that the strongly acidic cation exchange resin used herein was 1.2 mass part relative to the weakly basic anion exchange resin. The "chlorogenic acids composition" obtained was evaluated in the conditions described in [Evaluation Method 1].

Comparative Example 3

The solution A obtained in Preparation Example 1 was passed through a column packed with a strongly acidic cation exchange resin (trade name SK1BH, manufactured by Mitsubishi Chemical Corporation) at a flow rate of SV1 [hr$^{-1}$] in an amount of 20 mass part relative to the resin (1 mass part) to obtain a "chlorogenic acids composition" (pH=2.3). The "chlorogenic acids composition" obtained was evaluated in the conditions described in [Evaluation Method 1].

Comparative Example 4

The solution A obtained in Preparation Example 1 was passed through a column packed with a strongly acidic cation exchange resin (trade name SK1BH, manufactured by Mitsubishi Chemical Corporation) at a flow rate of SV1 [hr$^{-1}$] in an amount of 20 mass part relative to the resin (1 mass part). The pH of the solution after the pass was 2.3.

The solution was passed through a column packed with a porous resin (trade name Sepa beads SP207, manufactured by Mitsubishi Chemical Corporation) at a flow rate of SV1 [hr$^{-1}$] in an amount of 15 mass part relative to the resin (1 mass part). Subsequently, water was passed through the column at a flow rate of SV1 [hr$^{-1}$] in an amount of 2 mass part relative to the resin (1 mass part).

The porous resin used herein had been washed with ethanol and thereafter substituted with water.

Thereafter, an alkali solution (NaOH: 0.5 mass % solution) was passed through the column at SV5 [hr$^{-1}$] in an amount of 25 mass part relative to the resin (1 mass part). The solution was passed through the column packed with a strongly acidic cation exchange resin (trade name SK1BH, manufactured by Mitsubishi Chemical Corporation) and pH was adjusted to 3.1 to obtain a "chlorogenic acids composition". Note that the strongly acidic cation exchange resin used herein was 1.2 mass part relative to the porous resin. The "chlorogenic acids composition" obtained was evaluated in the conditions described in [Evaluation Method 1].

These results are shown in Table 2.

TABLE 2

| Step | Item | Unit | Example 1 | Example 2 | Example 3 | Example 4 | Example 5 | Example 6 | Example 7 | Example 8 |
|---|---|---|---|---|---|---|---|---|---|---|
| Starting material | Extract from green beans/roasted beans | [—] | Green beans | Green beans | Green beans | Green beans | Green beans | Green beans | Green beans | Green beans |
| Concentration of starting material | Concentration of starting material CGA | [%] | 1.2% | 1.2% | 1.2% | 1.2% | 1.2% | 1.2% | 1.2% | 3.6% |
| Step A | Cation exchange resin | [—] | Cation exchange resin | Cation exchange resin | Cation exchange resin | Cation exchange resin | Cation exchange resin | Cation exchange resin | Weakly acidic | Cation exchange resin |
| | pH after treatment | [—] | 2.3 | 3.0 | 2.7 | 3.3 | 2.3 | 2.3 | 3.3 | 2.0 |
| Step B, C | Treatment with anion exchange resin | present/absent | present | present | present | present | present | present | present | present |
| | Flow ratio | [BV] | 15 | 15 | 15 | 15 | 10 | 20 | 15 | 5 |
| Chlorogenic acids composition | Yield of chlorogenic acids composition | [%] | 90% | 76% | 78% | 58% | 92% | 91% | 70% | 90% |
| | Purity of chlorogenic acids | [%] | 72% | 70% | 71% | 62% | 73% | 72% | 78% | 72% |
| | Taste and flavor (coarseness) | [—] | 3.8 | 3.2 | 3.6 | 3.2 | 3.8 | 3.8 | 3.6 | 3.8 |
| | Taste and flavor (fresh sourness) | [—] | 3.8 | 3.8 | 3.8 | 3.6 | 3.8 | 3.8 | 3.8 | 3.8 |
| | Caffeine content ratio | [%] | 0.02% | 0.02% | 0.02% | 0.02% | 0.02% | 0.02% | 0.01% | 0.02% |
| | Chlorogenic acids content ratio | [%] | 0.78% | 0.53% | 0.67% | 0.50% | 0.79% | 0.78% | 0.60% | 0.77% |
| | Caffeine/chlorogenic acids ratio | [—] | 0.024 | 0.032 | 0.031 | 0.035 | 0.021 | 0.024 | 0.021 | 0.025 |
| | Sucrose/chlorogenic acids | [—] | 0.00 | 0.00 | 0.00 | 0.00 | 0.00 | 0.00 | 0.00 | 0.00 |
| | Protein/chlorogenic acids | [—] | 0.04 | 0.04 | 0.04 | 0.04 | 0.04 | 0.04 | 0.04 | 0.04 |
| | Citric acid/chlorogenic acids | [—] | 0.11 | 0.13 | 0.11 | 0.12 | 0.11 | 0.12 | 0.11 | 0.11 |
| | Malic acid/chlorogenic acids | [—] | 0.03 | 0.03 | 0.03 | 0.03 | 0.03 | 0.03 | 0.03 | 0.03 |
| | Quinic acid/chlorogenic acids | [—] | 0.05 | 0.05 | 0.04 | 0.05 | 0.05 | 0.05 | 0.05 | 0.05 |
| | pH | [—] | 3.1 | 3.2 | 3.1 | 3.2 | 3.1 | 3.1 | 3.1 | 3.1 |

| Step | Item | Unit | Example 9 | Example 10 | Comparative Example 1 | Comparative Example 2 | Comparative Example 3 | Comparative Example 4 |
|---|---|---|---|---|---|---|---|---|
| Starting material | Extract from green beans/roasted beans | [—] | Roasted beans | Green beans | Green beans | Green beans | Green beans | Green beans |
| Concentration of starting material | Concentration of starting material CGA | [%] | 1.2% | 0.75% | 1.2% | 1.2% | 1.2% | 1.2% |
| Step A | Cation exchange resin | [—] | Cation exchange resin | Cation exchange resin | None | None (acid added) | Cation exchange resin | Cation exchange resin |
| | pH after treatment | [—] | 2.0 | 2.4 | 5.7 | 2.3 | 2.3 | 2.3 |
| Step B, C | Treatment with anion exchange resin | present/absent | present | present | present | present | Absent | Absent (porous resin) |
| | Flow ratio | [BV] | 15 | 24 | 15 | 15 | 15 | 15 |
| Chlorogenic acids composition | Yield of chlorogenic acids composition | [%] | 91% | 88% | 41% | 50% | 99% | 56% |
| | Purity of chlorogenic acids | [%] | 66% | 70% | 49% | 54% | 50% | 72% |
| | Taste and flavor (coarseness) | [—] | 3.4 | 3.4 | 1.8 | 2.2 | 1.2 | 3.0 |
| | Taste and flavor (fresh sourness) | [—] | 3.8 | 3.8 | 2.6 | 2.6 | 2.8 | 2.8 |

TABLE 2-continued

|  |  |  |  |  |  |  |  |
|---|---|---|---|---|---|---|---|
| Caffeine content ratio | [%] | 0.02% | 0.02% | 0.01% | 0.02% | 0.28% | 0.01% |
| Chlorogenic acids content ratio | [%] | 0.78% | 0.77% | 0.27% | 0.34% | 1.25% | 0.43% |
| Caffeine/chlorogenic acids ratio | [—] | 0.022 | 0.026 | 0.047 | 0.048 | 0.220 | 0.024 |
| Sucrose/chlorogenic acids | [—] | 0.00 | 0.00 | 0.03 | 0.00 | 0.41 | 0.00 |
| Protein/chlorogenic acids | [—] | 0.09 | 0.05 | 0.05 | 0.03 | 0.12 | 0.01 |
| Citric acid/chlorogenic acids | [—] | 0.11 | 0.12 | 0.08 | 0.14 | 0.10 | 0.00 |
| Malic acid/chlorogenic acids | [—] | 0.03 | 0.03 | 0.02 | 0.03 | 0.03 | 0.00 |
| Quinic acid/chlorogenic acids | [—] | 0.08 | 0.04 | 0.02 | 0.03 | 0.03 | 0.00 |
| pH | [—] | 3.0 | 3.0 | 3.1 | 3.2 | 2.3 | 3.1 |

In each of the purified chlorogenic acids compositions of the present invention had a reduced amount of protein, a predetermined amount of citric acid, high purity of chlorogenic acids and a good taste and flavor. In contrast, in the case where pH adjustment is not performed before bringing a composition into contact with an anion exchange resin, the yield, content and purity of a chlorogenic acids composition were low, and taste and flavor were unsatisfactory (Comparative Example 1). In the case where pH was adjusted by adding an acid before bringing a composition into contact with an anion exchange resin, the purity of chlorogenic acids was low and taste and flavor were unsatisfactory (Comparative Example 2). In the case where a composition is treated only with a cation exchange resin, the content of caffeine cannot be reduced, the purity of chlorogenic acids was low and taste and flavor were unsatisfactory (Comparative Example 3). In the case where a composition was treated with a cation exchange resin and thereafter treated with a porous resin, the yield of chlorogenic acids was low (Comparative Example 4).

The invention claimed is:

1. A method for producing a purified chlorogenic acids composition, comprising
   (A) bringing a chlorogenic acids-containing composition into contact with a cation exchange resin;
   (B) bringing a liquid obtained in (A) into contact with a weakly basic anion exchange resin; and
   (C) bringing an aqueous alkaline solution into contact with the weakly basic anion exchange resin after (B) and providing said purified chlorogenic acids.

2. The producing method according to claim 1, wherein the liquid obtained in (A) has a pH value of smaller than 4.

3. The producing method according to claim 1, wherein the liquid obtained in (A) has a pH value of from 0.5 to 3.5.

4. The producing method according to claim 1, further comprising (D) adjusting pH of the liquid obtained in (C) to from 2 to 7.

5. The producing method according to claim 1, further comprising (D) adjusting pH of the liquid obtained in (C) to from 2 to 5.

6. The producing method according to claim 1, further comprising, between (B) and (C), (E) bringing water into contact with the weakly basic anion exchange resin.

7. The producing method according to claim 1, wherein the aqueous alkaline solution used in (C) is an aqueous sodium hydroxide solution.

8. The producing method according to claim 1, wherein the chlorogenic acids-containing composition is a coffee bean extract.

9. The producing method according to claim 1, wherein, in (B), the liquid obtained in (A) is passed through the weakly basic anion exchange resin in a flow ratio of from 1 to 240 [mL/mL].

10. The producing method according to claim 1, wherein, in (B), the liquid obtained in (A) is passed through the weakly basic anion exchange resin in a flow ratio of from 1 to 30 [mL/mL].

11. The producing method according to claim 1, wherein, in (B), the liquid obtained in (A) is passed through the weakly basic anion exchange resin at a space velocity of from 0.1 to 50 [hr$^{-1}$].

12. The producing method according to claim 1, wherein, in (B), the liquid obtained in (A) is passed through the weakly basic anion exchange resin at a space velocity of from 0.1 to 10 [hr−1].

13. The producing method according to claim 1, wherein a concentration of chlorogenic acids in the chlorogenic acids-containing composition is from 0.1 to 20 mass %.

* * * * *